(12) United States Patent
Potyrailo et al.

(10) Patent No.: US 9,494,541 B2
(45) Date of Patent: Nov. 15, 2016

(54) SENSORS FOR GAS DOSIMETRY

(75) Inventors: Radislav Alexandrovich Potyrailo, Niskayuna, NY (US); Hubert Tunchiao Lam, Clifton Park, NY (US); Zhexiong Tang, Niskayuna, NY (US); Nandini Nagraj, Clifton Park, NY (US)

(73) Assignee: General Electricity Company, Schenectady, NY (US)

( * ) Notice: Subject to any disclaimer, the term of this patent is extended or adjusted under 35 U.S.C. 154(b) by 574 days.

(21) Appl. No.: 13/542,504

(22) Filed: Jul. 5, 2012

(65) Prior Publication Data

US 2014/0011286 A1 Jan. 9, 2014

(51) Int. Cl.
| | |
|---|---|
| G01N 27/00 | (2006.01) |
| G01N 27/02 | (2006.01) |
| G01N 33/00 | (2006.01) |
| G01N 33/543 | (2006.01) |
| G01N 27/327 | (2006.01) |
| B82Y 30/00 | (2011.01) |

(52) U.S. Cl.
CPC ........ *G01N 27/025* (2013.01); *G01N 33/0031* (2013.01); *B82Y 30/00* (2013.01); *G01N 27/3271* (2013.01); *G01N 33/5438* (2013.01)

(58) Field of Classification Search
CPC ..................... G01N 27/3271; G01N 33/5438; G01N 27/414; G01N 33/54373; G01N 27/126; G01N 33/0031; B82Y 15/00; B82Y 30/00
USPC ..................... 422/82.01, 82.02, 98
See application file for complete search history.

(56) References Cited

U.S. PATENT DOCUMENTS

| | | | | |
|---|---|---|---|---|
| 6,004,442 A | * | 12/1999 | Choulga | G01N 27/3275 204/415 |
| 6,200,444 B1 | * | 3/2001 | Ahlers | G01N 31/221 204/416 |
| 2007/0090926 A1 | | 4/2007 | Potyrailo et al. | |
| 2007/0090927 A1 | | 4/2007 | Potyrailo et al. | |
| 2007/0266770 A1 | * | 11/2007 | Denq | G01N 27/126 73/31.05 |
| 2009/0053104 A1 | | 2/2009 | Buttner et al. | |

(Continued)

FOREIGN PATENT DOCUMENTS

| | | |
|---|---|---|
| JP | 2007205744 | 8/2007 |
| JP | 2009036526 | 2/2009 |

(Continued)

OTHER PUBLICATIONS

Virji, Shabnam et al., Direct Electrical Measurement of the Conversion of Metal Acetates to Metal Sulfides by Hydrogen Sulfide, Inorganic Chemistry, Nov. 23, 2006, pp. 10467-10471, vol. 45, No. 26.

(Continued)

*Primary Examiner* — Krishnan S Menon
*Assistant Examiner* — Dwan A Gerido
(74) *Attorney, Agent, or Firm* — Jean K. Testa; Fletcher Yoder, P.C.

(57) ABSTRACT

Methods and sensors for selective fluid sensing are provided. A gas dosimeter includes a housing configured with an opening to admit an analyte. The gas dosimeter also includes a multivariate sensor disposed in the housing. The sensor is configured to determine a concentration of the analyte over time. In addition, the multivariate sensor includes an irreversible sensing material. Electrical properties of the irreversible sensing material are configured to change irreversibly upon exposure to the analyte.

21 Claims, 4 Drawing Sheets

(56) References Cited

U.S. PATENT DOCUMENTS

| | | | |
|---|---|---|---|
| 2010/0059375 A1* | 3/2010 | Weiller et al. | 204/433 |
| 2011/0003279 A1* | 1/2011 | Patel | 435/5 |
| 2011/0287551 A1 | 11/2011 | Weiller et al. | |
| 2012/0116683 A1* | 5/2012 | Potyrailo et al. | 702/19 |

FOREIGN PATENT DOCUMENTS

| | | |
|---|---|---|
| WO | 03021252 A1 | 3/2003 |
| WO | 2007014710 A2 | 2/2007 |

OTHER PUBLICATIONS

Virji, Shabnam et al., Polyaniline Nanofiber Composites with Metal Salts: Chemical Sensors for Hydrogen Sulfide, Small, 2005, pp. 624-627, vol. 1, No. 6.

Wohltjen, H. et al., Colloidal Metal-Insulator-Metal Ensemble Chemiresistor Sensor, Anal. Chem., 1998, 70, pp. 2856-2859.

Wang, L. et al., Flexible Chemiresistor sensors: Thin Film Assemblies of Nanoparticles on a Polyethylene Terephthalate substrate, J. Mater. Chem., 2010, pp. 907-991, vol. 20.

Josse, F. et al., AC-Impedance-Based Chemical Sensors for Organic Solvent Vapors, Sens. Actuators B, 1996, pp. 363-369, vol. 35-36.

Amrani, M. E. H. et al., Multi-Frequency Measurements of Organic Conducting Polymers for Sensing of Gases and Vapours, Sens. Actuators B, 1996, pp. 137-141, vol. 33.

Janata, J., Electrochemical Sensors and Their Impedances: a Tutorial, Crit. Rev. Anal. Chem., 2002, pp. 109-120, vol. 32.

Pejcic, B. et al., Impedance Spectroscopy: Over 35 years of Electrochemical Sensor Optimization, Electrochim. Acta, 2006, pp. 6217-6229, vol. 51.

Yang, R. D. et al., Chemical Identification Using an Impedance Sensor Based on Dispersive Charge Transport, Appl. Phys. Lett., 2006, pp. 74-104, vol. 88.

Amrani, M. E. H. et al., Multi-Frequency Interrogation Technique Applied to Conducting Polymer Gas and Odour Sensors, IEE Proc.-Sci. Meas. Technol., 1999, pp. 95-101, vol. 146.

Wise, K. D. et al., Microfabrication Techniques for Integrated Sensors and Microsystems, Science, 1991, pp. 1335-1342, vol. 254.

Armani, A. M. et al., Label-Free, Single-Molecule Detection with Optical Microcavities, Science, 2007, pp. 783-787, vol. 317.

Rose, A. et al., Sensitivity Gains in Chemosensing by Lasing Action in Organic Polymers, Nature, 2005, pp. 876-879, vol. 434.

U.S. Appl. No. 12/942,732, filed Nov. 9, 2010, Potyrailo et al.

U.S. Appl. No. 12/977,568, filed Dec. 23, 2010, Potyrailo et al.

U.S. Appl. No. 12/977,599, filed Dec. 23, 2010, Potyrailo et al.

Potyrailo, R. A; Surman, C.; Go, S.; Lee, Y.; Sivavec, T.; Morris, W. G., Development of radio-freguency identification sensors based on organic electronic sensing materials for selective detection of toxic vapors, J. Appl. Phys. 2009, 106, 124902.

Grate, J. W.; McGill, R. A., Dewetting effects on polymer-coated surface acoustic wave vapor sensors, Anal. Chem. 1995, 67, 4015-4019.

Mabrook, M. F.; Pearson, C.; Petty, M. C., An inkjet-printed chemical fuse, Appl. Phys. Lett. 2005, 86, 013507-1-013507-3.

\* cited by examiner

SENSORS FOR GAS DOSIMETRY

BACKGROUND

The subject matter disclosed herein relates to chemical and biological sensors, and more particularly, to chemical and biological sensors for gas dosimetry.

Chemical and biological sensors are often employed in a number of applications where the detection of various vapors may be used to discern useful information. For instance, measuring the presence of vapors by discerning a change in certain environmental variables within or surrounding a sensor may be particularly useful in monitoring changes in biopharmaceutical products, food or beverages, monitoring industrial areas for chemical or physical hazards, as well as in security applications, such as residential home monitoring, home land security in airports, in different environmental and clinical settings, and other public venues wherein detection of certain harmful and/or toxic vapors may be particularly useful. In addition, it may be desirable to measure the concentration of a vapor over time, which may be referred to as dosimetry.

One technique for sensing such environmental changes is by employing a sensor, such as an RFID sensor, coated with a particular sensing material. In addition, sensors may be arranged in an array of individual transducers, which are coated with one or more sensing materials. Many sensor arrays include a number of identical sensors. However, while using identical sensors simplifies fabrication of the sensor array, such an array may have limited capabilities for sensing only a single response (e.g. resistance, current, capacitance, work function, mass, optical thickness, light intensity, etc). In certain applications multiple responses or changes in multiple properties may occur. In such applications, it may be beneficial to include an array of sensors wherein different transducers in the array employ the same or different responses (e.g. resistance, current, capacitance, work function, mass, optical thickness, light intensity, etc.) and are coated with different sensing materials such that more than one property can be measured. Disadvantageously, fabricating a sensor array having individual sensors uniquely fabricated to sense a particular response, complicates fabrication of the array.

Further, in many practical applications, it is beneficial to use highly selective chemical and biological sensors. That is, it is often desirable to provide a sensor array capable of sensing multiple vapors and vapor mixtures in the presence of other vapors and mixtures. The greater the number of vapors and vapor mixtures that may be present, the more difficult it may be to accurately sense and discern a specific type of vapor or vapor mixture being sensed. This may be particularly true when one or more vapors are present at levels of magnitude greater than the other vapors of interest for detection. For instance, the presence of certain contaminants may interfere with the accurate measurement of a specific vapor.

Various embodiments disclosed herein may address one or more of the challenges set forth above.

BRIEF DESCRIPTION

In accordance with one embodiment, there is provided a gas dosimeter that includes a housing configured with an opening to admit an analyte. The gas dosimeter also includes a multivariate sensor disposed in the housing. The sensor is configured to determine a concentration of the analyte over time. In addition, the multivariate sensor includes an irreversible sensing material. Electrical properties of the irreversible sensing material are configured to change irreversibly upon exposure to the analyte.

In accordance with another embodiment, there is provided a multivariate sensor that includes an irreversible sensing material. The irreversible sensing material includes a first matrix configured to provide a first output indicative of the concentration of an analyte over time and a second matrix configured to provide a second output to correct for environmental interference effects. Electrical properties of the irreversible sensing material are configured to change irreversibly upon exposure to the analyte.

In accordance with another embodiment, there is provided a method of irreversibly measuring a concentration of an analyte over time. The method includes measuring a real part and an imaginary part of an impedance spectrum of a resonant sensor antenna coated with an irreversible sensing material, calculating at least six spectral parameters of the resonant sensor antenna coated with the irreversible sensing material, reducing the impedance spectrum or the calculated spectral parameters to a single data point using multivariate analysis to selectively determine the concentration of the analyte, and determining one or more environmental parameters from the impedance spectrum.

In accordance with another embodiment, a multivariate dosimeter sensor includes at least two transducers configured to generate at least two signals, an irreversible sensing material disposed on the at least two transducers, and an RFID device comprising an integrated circuit chip configured to receive the at least two signals.

In accordance with another embodiment, a multivariate dosimeter sensor node includes a first transducer configured to generate a first signal, a second transducer configured to generate a second signal, a sensing material disposed on both the first transducer and the second transducer, and an RFID device comprising an integrated circuit chip configured to receive the first and second signals.

In accordance with another embodiment, a method for manufacturing a multivariate dosimeter sensor includes providing a sensor substrate with a controllable surface energy and depositing a nonpatterned or patterned irreversible sensing film onto the sensor substrate. The nonpatterned or patterned irreversible sensing film is configured to promote dewetting and coalescence effects of the nonpatterned or patterned irreversible sensing film.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
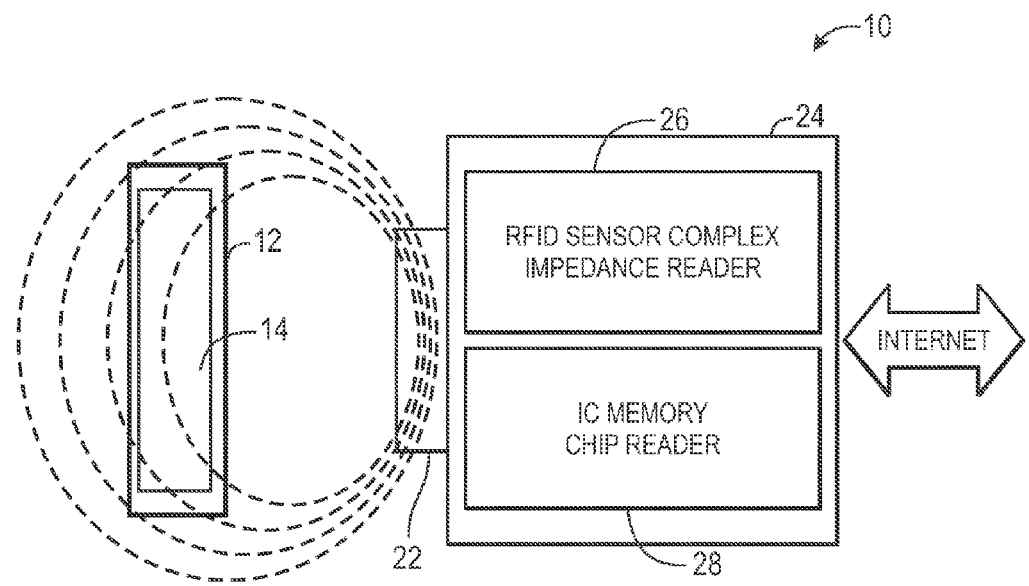
FIG. 1 illustrates a sensing system, in accordance with embodiments of the invention.

Embodiments disclosed herein provide methods and systems for irreversible selective vapor sensing for gas dosimetry wherein a single sensor is provided and is capable of detecting multiple vapors and/or mixtures of vapors alone, or in the presence of one another. Examples of general methods for vapor sensing using a single sensor are described in U.S. Patent Publication No. 2012/0116683 entitled "Highly Selective Chemical and Biological Sensors," which is incorporated herein by reference. The disclosed sensors are capable of detecting different vapors and mixtures even in the presence of various contaminants or an environment wherein one or more vapors has a substantially higher concentration (e.g. 10×) compared to other components in the mixture. In certain embodiments, the sensor includes a resonant inductor (L)—capacitor (C)—resistor (R) (LCR) sensor that is coated with an irreversible sensing material, which may be defined as a material that changes its properties, such as its electrical, morphological, dimensional, aggregation, physical, chemical, and other properties, irreversibly during analyte sensing. For example, the electrical properties of such irreversible sensing materials may not return to their original values upon removal of the analyte, or vapor of interest. In other words, irreversible sensing materials may provide a cumulative measurement of the vapor of interest over time. Such irreversible sensing materials may have greater sensitivity to low concentrations of vapors than reversible sensing materials. In addition, embodiments of gas dosimeters using irreversible sensing materials may have greater selectivity and tunability of chemistries than conventional gas dosimeters, may have shorter acquisition times than conventional gas dosimeters, and may be trackable (e.g., capable of providing analyte concentration over time).

In various embodiments, the irreversible sensing material may be disposed between electrodes of a sensor or on a surface of a device that is configured as a resonant circuit, such as an LCR sensor. Non-limiting examples of LCR sensors include RFID sensors with an integrated circuit (IC) memory chip, RFID sensors with an IC chip, and RFID sensors without an IC memory chip (chipless RFID sensors or chipless LCR sensors). LCR sensors can be wireless or wired. In order to collect data, an impedance spectrum is acquired over a relatively narrow frequency range, such as the resonant frequency range of the LCR circuit. The technique further includes calculating the multivariate signature from the acquired spectrum and manipulating the data to discern the presence of certain vapors and/or vapor mixtures. The presence of vapors is detected by measuring the changes in dielectric, dimensional, charge transfer, and other changes in the properties of the materials employed by observing the changes in the resonant electronic properties of the circuit. By using a mathematical procedure, such as principal component analysis (PCA) and others known in the art, multiple vapors and mixtures can be detected in the presence of one another and in the presence of an interferent as further described below. Thus, several responses from a single sensor to a measured environment may provide complementary information and serve to correct for environmental interference effects. Embodiments disclosed herein provide methods and systems for irreversible selective fluid sensing wherein a single sensor is provided and is capable of detecting multiple fluids and/or mixtures of fluids alone, or in the presence of one another.

To more clearly and concisely describe the subject matter of the claimed invention, the following definitions are provided for specific terms, which are used in the following description and the appended claims.

The term "fluids" includes gases, vapors, liquids, and solids.

The term "gas dosimetry" includes monitoring the concentration of an analyte over time and may be used in a variety of monitoring applications including, but not limited to, air and environment monitoring for toxic gases and vapors, detection of explosives (e.g., vapors leaking from cargo containers in transit), detection of food spoilage (e.g., vapors evolving during food storage), detection of volatile organic compounds (VOCs) (e.g., volatile organic chemicals, toxic gases, or vapors evolving during storage of chemicals), detection of feces or flatulence (i.e., personal care monitoring), occupational exposure monitoring, air or water monitoring, regulatory monitoring, and so forth. The term "gas dosimeter" refers to a device capable of performing gas dosimetry.

The term "analyte" includes any substance or chemical constituent that is the subject of a chemical analysis, such as gas dosimetry. Examples of analytes include, but are not limited to, acidic or basic gases, oxidant or reducing gases, other gases, or any combination thereof. Examples of acidic or basic gases include, but are not limited to, ammonia, hydrogen sulfide, methanethiol, hydrogen bromide, hydrogen chloride, hydrogen iodide, hydrogen fluoride, and so forth. Examples of oxidant or reducing gases include, but are not limited to, hydrogen peroxide, chlorine dioxide, oxygen, chlorine, bromine, and so forth. Examples of other gases include, but are not limited to, sulfur dioxide, arsine, hydrogen cyanide, phosgene, triacetone triperoxide, carbon dioxide, carbon monoxide, trinitrotoluene, explosives, and so forth.

The term "digital ID" includes all data stored in a memory chip of the RFID sensor. Non-limiting examples of this data are manufacturer identification, electronic pedigree data, user data, and calibration data for the sensor.

The term "monitoring process" includes, but is not limited to, measuring physical changes that occur around the sensor. For example, monitoring processes including monitoring changes in a biopharmaceutical, food or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of irreversible sensing material and transducer geometry to enhance the selectivity of the sensor in dynamic and steady state measurements of individual vapors and their mixtures.

The term "environmental parameters" is used to refer to measurable environmental variables within or surrounding a manufacturing or monitoring system. The measurable environmental variables comprise at least one of physical, chemical, and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

The term "interference" includes any undesired environmental parameter that undesirably affects the accuracy and precision of measurements with the sensor. The term "interferent" refers to a fluid or an environmental parameter (that includes, but is not limited to temperature, pressure, light, etc.) that potentially may produce an interference response by the sensor.

The term "multivariate analysis" refers to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. The term "principal components analysis (PCA)" refers to a mathematical procedure that is used to reduce multidimensional data sets to lower dimensions for analysis. Principal components analysis is a part of eigenanalysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "spectral parameters" is used to refer to measurable variables of the sensor response. The sensor response is the impedance spectrum of the resonance sensor circuit of the LCR or RFID sensor. In addition to measuring the impedance spectrum in the form of Z-parameters, S-parameters, and other parameters, the impedance spectrum (its both real and imaginary parts) may be analyzed simultaneously using various parameters for analysis, such as, the frequency of the maximum of the real part of the impedance ($F_p$), the magnitude of the real part of the impedance ($Z_p$), the resonant frequency of the imaginary part of the impedance ($F_1$), and the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency ($F_z$, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra, are called here "features" or "descriptors." The appropriate selection of features is performed from all potential features that can be calculated from spectra. Multivariable spectral parameters are described in U.S. Pat. No. 7,911,345 entitled "Methods and systems for calibration of RFID sensors," which is incorporated herein by reference.

The term "resonance impedance" or "impedance" refers to measured sensor frequency response as real and imaginary parts of impedance around the resonance of the sensor from which the sensor "spectral parameters" are extracted.

The term "protecting material" includes, but is not limited to, materials on the LCR or RFID sensor that protect the sensor from an unintended mechanical, physical or chemical effect while still permitting the anticipated measurements to be performed. For example, an anticipated measurement may include solution conductivity measurement wherein a protecting film separates the sensor from the liquid solution yet allows an electromagnetic field to penetrate into solution. An example of a protecting material is a paper film that is applied on top of the sensor to protect the sensor from mechanical damage and abrasion. Another non-limiting example of a protecting material is a polymer film that is applied on top of the sensor to protect the sensor from corrosion when placed in a liquid for measurements. A protecting material may also be a polymer film that is applied on top of the sensor for protection from shortening of the sensor's antenna circuit when placed in a conducting liquid for measurements. Non-limiting examples of protecting films are paper, polymeric, and inorganic films such as polyesters, polypropylene, polyethylene, polyethers, polycarbonate, polyethylene terephthalate, zeolites, metal-organic frameworks, and cavitands. The protecting material can be arranged between the transducer and sensing film to protect the transducer. The protecting material can be arranged on top of the sensing film which is itself is on top of the transducer to protect the sensing film and transducer. The protecting material (e.g., a filter layer) on top of the sensing film which is itself is on top of the transducer can serve to as a filter material to protect the sensing film from exposure to gaseous or ionic interferences. Non-limiting examples of filter materials include zeolites, metal-organic frameworks, and cavitands.

As used herein the term "sensing materials and sensing films" includes, but is not limited to, materials deposited onto a transducer's electronics module, such as LCR circuit components or an RFID tag, to perform the function of predictably and reproducibly affecting the impedance sensor response upon interaction with the environment. In order to prevent the material in the sensor film from leaching into the liquid environment, the sensing materials are attached to the sensor surface using standard techniques, such as covalent bonding, electrostatic bonding, and other standard techniques known to those of ordinary skill in the art.

"Composites" are materials made from two or more constituent materials with significantly different physical or chemical properties, which remain separate and distinct on a macroscopic level within the finished structure. Non-limiting examples of composites include carbon black composites. "Nanocomposites" are materials made from two or more constituent materials with significantly different physical or chemical properties, which remain separate and distinct on a nanoscale level within the finished structure. Non-limiting examples of nanocomposites include: carbon nanotube nanocomposites; semiconducting nanocrystal quantum dot nanocomposites, metal oxide nanowires, and carbon nanotubes; metal nanoparticles or nanoclusters functionalized with carbon nanotubes.

The terms "transducer and sensor" are used to refer to electronic devices such as RFID and LCR devices intended for sensing. "Transducer" is a device before it is coated with a sensing or protecting film or before it is calibrated for a sensing application. "Sensor" is a device typically after it is coated with a sensing or protecting film and after being calibrated for the sensing application.

As used herein the term "RFID tag" refers to an identification and reporting technology that uses electronic tags for identifying and/or tracking articles to which the RFID tag may be attached. An RFID tag typically includes at least two components where the first component is an integrated circuit (IC) memory chip for storing and processing information and modulating and demodulating a radio frequency signal. This memory chip can also be used for other specialized functions, for example, it can contain a capacitor. It can also contain at least one input for an analog signal such as resistance input, capacitance input, or inductance input. In the case of a chipless RFID tag, the RFID tag may not include an IC memory chip. This type of RFID tag may be useful in applications where a specific RFID tag does not need to be identified, but rather a signal merely indicating the presence of the tag provides useful information (e.g., product security applications). The second component of the RFID tag is an antenna for receiving and transmitting the radio frequency signal.

The term "RFID sensor" is an RFID tag with an added sensing function as, for example, when an antenna of the RFID tag also performs sensing functions by changing its impedance parameters as a function of environmental changes. The accurate determinations of environmental changes with such RFID sensors are performed by analysis of resonance impedance. For example, RFID tags may be converted into RFID sensors by coating the RFID tag with a sensing film. By coating the RFID tag with a sensing film, the electrical response of the film is translated into simultaneous changes to the impedance response, resonance peak position, peak width, peak height and peak symmetry of the impedance response of the sensor antenna, magnitude of the real part of the impedance, resonant frequency of the imaginary part of the impedance, anti-resonant frequency of the imaginary part of the impedance, zero-reactance frequency, phase angle, and magnitude of impedance, and others as described in the definition of the term sensor "spectral parameters." The "RFID sensor" can have an integrated circuit (IC) memory chip attached to the antenna or can have no IC memory chip. An RFID sensor without an IC memory chip is an LCR sensor. An LCR sensor is comprised of known components, such as at least one inductor (L), at least one capacitor (C), and at least one resistor (R) to form an LCR circuit.

The term "single-use container" includes, but is not limited to, packaging, manufacturing, or monitoring equipment, which may be disposed of after use or reconditioned for reuse. Single-use packaging in the food industry includes, but is not limited to, food and drinks packaging, and candy and confection boxes. Single-use monitoring components include, but are not limited to, single-use cartridges, dosimeters, and collectors. Single use manufacturing containers include, but are not limited to, single-use vessels, bags, chambers, tubing, connectors, and columns.

The term "writer/reader" includes, but is not limited to, a combination of devices to write and read data into the memory of the memory chip and to read impedance of the antenna. Another term for "writer/reader" is "interrogator."

In accordance with embodiments disclosed herein, an LCR or an RFID sensor for sensing vapors, vapor mixtures, and biological species is described. As previously described, the RFID sensor includes an RFID tag coated with an irreversible sensing material. In one embodiment, a passive RFID tag may be employed. As will be appreciated, an RFID tag may include an IC memory chip, which is connected to an antenna coil for communication with a writer/reader. The IC memory chip can be read by illuminating the tag by a radio frequency (RF) and/or microwave carrier signal sent by the writer/reader. When the RF and/or microwave field passes through the antenna coil, an AC voltage is generated across the coil. The voltage is rectified in the microchip to result in a DC voltage for the microchip operation. The IC memory chip becomes functional when the DC voltage reaches a predetermined level. By detecting the RF and/or microwave signal backscattered from the microchip, the information stored in the microchip can be fully identified. The distance between the RFID tag/sensor and the writer/reader is governed by the design parameters that include operating frequency, RF and/or microwave power level, the receiving sensitivity of the reader/writer, antenna dimensions, data rate, communication protocol, and microchip power requirements. The distance between the "RFID sensor" without an IC memory chip (chipless RFID sensor or LCR sensor or LCR transducer) and the sensor reader is governed by the design parameters that include operating frequency, RF or microwave power level, the receiving sensitivity of the sensor reader, and antenna dimensions.

In one embodiment a passive RFID tag with or without an IC memory chip may be employed. Advantageously, a passive RFID tag does not rely on a battery for operation. However, the communication distance between the writer/reader and RFID tag is typically limited within a proximity distance because the passive tag operates with only microwatts of RF power from the writer/reader. For passive tags operating at 13.56 MHz, the read distance is typically not more than several centimeters. The typical frequency range of operation of 13.56 MHz passive RFID tags for digital ID writing/reading is from 13.553 to 13.567 MHz. The typical frequency range of operation of 13.56-MHz passive RFID sensors for sensing of environmental changes around the RFID sensor is from about 5 MHz to about 20 MHz, more preferably from 10 to 15 MHz. The requirement for this frequency range is to be able to recognize the tag with a writer/reader that operates at 13.56 MHz while the sensor portion of the RFID tag operates from 5 to 20 MHz.

Depositing sensing films onto passive RFID tags creates RFID chemical or biological sensors. RFID sensing is performed by measuring changes in the RFID sensor's impedance as a function of environmental changes around the sensor, as described further below. If the frequency response of the antenna coil, after deposition of the sensing film, does not exceed the frequency range of operation of the tag, the information stored in the microchip can be identified with a conventional RFID writer/reader. An impedance or network analyzer (sensor reader) can read the impedance of the antenna coil to correlate the changes in impedance to the chemical and biological species of interest and to physical, chemical, or/and biological changes of environmental parameters around the sensor.

In operation, after coating of the RFID tag with a chemically sensitive film, both the digital tag ID and the impedance of the tag antenna may be measured. The measured digital ID provides information about the identity of the tag itself, such as an object onto which this tag is attached, and the properties of the sensor (e.g. calibration curves for different conditions, manufacturing parameters, expiration date, etc.). For multi-component detection, multiple properties from the measured real and imaginary portions of the impedance of a single RFID sensor may be determined, as described further below.

In summary, and in accordance with the embodiments described herein, in order to achieve high selectivity detection of analytes in the presence of high levels of interferences, the sensor should exhibit a number of characteristics. First, the selected transducer should include a multivariate output to independently detect the effects of different environmental parameters on the sensor. Second, the irreversible sensing material should have a preserved magnitude of response to an analyte over a wide concentration range of an interferent. The response to the relatively small analyte concentrations should not be fully suppressed by the presence of the relatively high concentrations of the interferents. Third, the response of the irreversible sensing material to interference species is allowed and may exist but should not compete with the response to the analyte and should be in a different direction of the multivariate output response of the transducer.

To achieve these characteristics, in one embodiment, the irreversible sensing material has multiple response mechanisms to vapors where these response mechanisms are related to the changes of dielectric constant, resistance, and swelling of the irreversible sensing material where these changes are not fully correlated with each other and produce different patterns upon exposure to individual vapors and their mixtures. Further, the LCR transducer can have multiple components of LCR response from the LCR circuit where these multiple components of LCR response originate from the different factors affecting the transducer circuit with the non-limiting examples that include material resistance and capacitance, contact resistance and capacitance between the transducer and irreversible sensing material, and resistance and capacitance between the transducer substrate and irreversible sensing material. Further, the LCR transducer can have multiple conditions of LCR circuit operation where an integrated circuit chip is a part of the sensor circuit.

Figure 2:
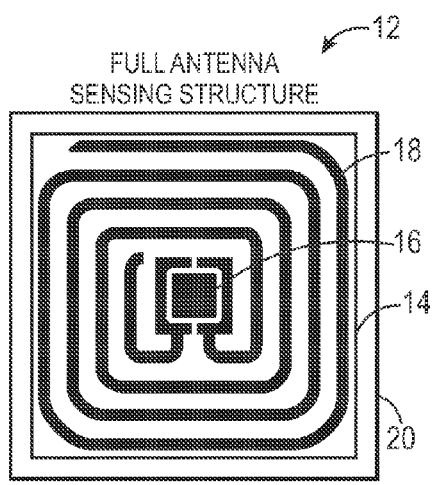
FIG. 2 illustrates an RFID sensor, in accordance with embodiments of the invention.

Turning now to the figures and referring initially to FIG. 1, a sensing system 10 is provided to illustrate the principle of selective vapor sensing utilizing an RFID sensor 12 having an irreversible sensing material 14 coated thereon. Referring briefly to FIG. 2, the sensor 12 is a resonant circuit that includes an inductor-capacitor-resistor structure (LCR) coated with the irreversible sensing material 14. In other words, the sensor 12 may be described as a multivariable sensor transducer. The irreversible sensing material 14 is applied onto the sensing region between the electrodes, which form sensor antenna 18 that constitute the resonant circuit. As will be described further below, by applying the irreversible sensing material 14 onto the resonant circuit, the impedance response of the circuit will be altered. The sensor 12 may be a wired sensor or a wireless sensor. The sensor 12 may also include a memory chip 16 coupled to resonant antenna 18 that is coupled to a substrate 20. The memory chip 16 may include manufacturing, user, calibration and/or other data stored thereon. The memory chip 16 is an integrated circuit device and it includes RF signal modulation circuitry fabricated using a complementary metal-oxide semiconductor (CMOS) process and a non-volatile memory. The RF signal modulation circuitry components include a diode rectifier, a power supply voltage control, a modulator, a demodulator, a clock generator, and other components.

Figure 3:
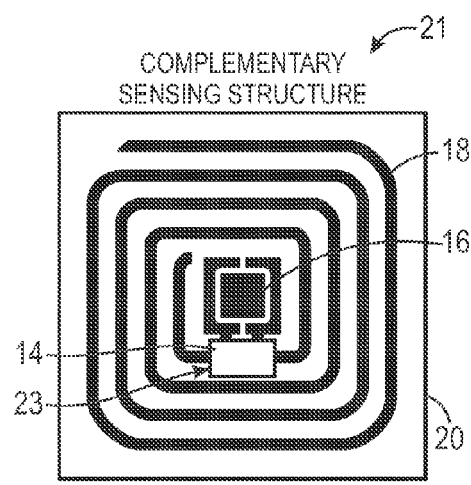
FIG. 3 illustrates an RFID sensor, in accordance with alternate embodiments of the invention.

FIG. 3 illustrates an alternative embodiment of the sensor 12, designated by reference numeral 21, wherein a complementary sensor 23 comprising the irreversible sensing material 14 is attached across the antenna 18 and the integrated circuit (IC) memory chip 16 to alter the sensor impedance response. In another embodiment (not illustrated), a complementary sensor may be attached across an antenna that does not have an IC memory chip and alters sensor impedance response. Non-limiting examples of complementary sensors are interdigitated sensors, resistive sensors, and capacitive sensors. Complementary sensors are described in U.S. Pat. No. 7,911,345 entitled "Methods and systems for calibration of RFID sensors," which is incorporated herein by reference.

In one embodiment, a 13.56 MHz RFID tag may be employed. During operation of the sensing system 10, the impedance Z(f) of the sensor antenna 18 and the digital sensor calibration parameters stored on the memory chip 16 may be acquired. Referring again to FIG. 1, measurement of the resonance impedance Z(f) of the antenna 18 and the reading/writing of digital data from the memory chip 16 are performed via mutual inductance coupling between the RFID sensor antenna 18 and the pickup coil 22 of a reader 24. As illustrated, the reader 24 may include an RFID sensor impedance reader 26 and an integrated circuit memory chip reader 28. The interaction between the RFID sensor 12 and the pickup coil 22 can be described using a general mutual inductance coupling circuit model. The model includes an intrinsic impedance $Z_C$ of the pickup coil 22 and an intrinsic impedance $Z_S$ of the sensor 12. The mutual inductance coupling B and the intrinsic impedances $Z_C$ and $Z_S$ are related through the total measured impedance $Z_T$ across the terminal of the pickup coil 22, as represented by the following equation:

$$Z_T = Z_C + (\omega^2 B^2 / Z_S), \tag{1}$$

wherein $\omega$ is the radian carrier frequency and B is the mutual inductance coupling B coefficient.

Sensing is performed via monitoring of the changes in the properties of the irreversible sensing material 14 as probed by the electromagnetic field generated in the antenna 18 (FIG. 2). Upon reading the RFID sensor 12 with the pickup coil 22, the electromagnetic field generated in the sensor antenna 18 extends out from the plane of the sensor 12 and is affected by the dielectric property of an ambient environment providing the opportunity for measurements of physical, chemical, and biological parameters.

Similarly, sensing is performed via monitoring of the changes in the properties of the irreversible sensing material 14 as probed by the electromagnetic field generated in the complementary sensor 23 (FIG. 3). Upon reading the RFID sensor 12 with the pickup coil 22, the electromagnetic field generated in the complementary sensor 23 extends out from the plane of the complementary sensor 23 and is affected by the dielectric property of an ambient environment providing the opportunity for measurements of physical, chemical, and biological parameters.

Figure 4:
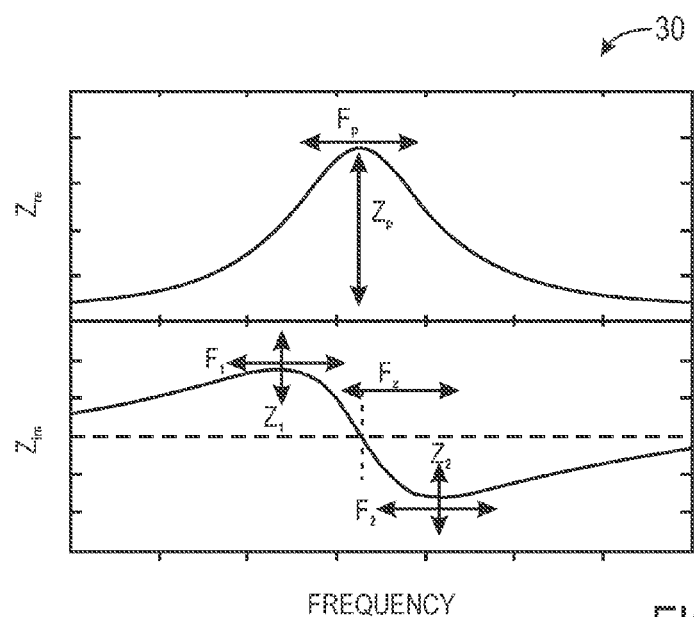
FIG. 4 illustrates measured responses of an RFID sensor, in accordance with embodiments of the invention.

FIG. 4 illustrates an example of measured responses of an exemplary RFID sensor 12, in accordance with embodiments of the invention, which includes the sensor's full impedance spectra and several individually measured spectral parameters. To selectively detect several vapors or fluids using a single RFID sensor, such as the RFID sensor 12, the real $Z_{re}(f)$ and imaginary $Z_{im}(f)$ parts of the impedance spectra $Z(f)=Z_{re}(f)+jZ_{im}(f)$ are measured from the sensor antenna 18 coated with an irreversible sensing material and at least four spectral parameters are calculated from the measured $Z_{re}(f)$ and $Z_{im}(f)$, as illustrated in the plot 30 of FIG. 4. Seven spectral parameters can be calculated as illustrated in the plot 30 of FIG. 4. These parameters include the frequency position $F_p$ and magnitude $Z_p$ of $Z_{re}(f)$, the resonant $F_1$ and anti-resonant $F_2$ frequencies of $Z_{im}(f)$, the impedance magnitudes $Z_1$ and $Z_2$ at $F_1$ and $F_2$ frequencies, respectively, and the zero-reactance frequency $F_Z$. Additional parameters, such as quality factor may also be calculated. From the measured parameters, resistance R, capacitance C, and other parameters of the sensing film-coated resonant antenna 18 can be also determined. Multivariate analysis may be used to reduce the dimensionality of the impedance response, either from the measured real $Z_{re}(f)$ and imaginary $Z_{im}(f)$ parts of the impedance spectra or from the calculated parameters $F_p$, $Z_p$, $F_1$ and $F_2$, and possibly other parameters to a single data point in multi-dimensional space for selective quantization of different vapors or fluids, as will be appreciated by those skilled in the art, and as will be described further below.

The presence of even relatively low levels of interferences (0.1-10 fold overloading levels) represents a significant limitation for individual sensors due to their insufficient selectivity. This problem can be addressed with an introduction of a concept of sensor arrays. Unfortunately, in practical situations (e.g. urban, environmental, and workplace monitoring, breath analysis, and others), sensor arrays suffer from interference effects at high ($10^2$-$10^6$ fold) overloading levels. These interference effects reduce the use of both sensors and sensor arrays. Advantageously, embodiments described herein provide techniques to overcome these two key scientific limitations of existing sensors and sensor arrays, such as difficulty or inability of operating with high overloading from interferences and of selective measurements of multiple vapors and their mixtures using a single sensor.

The well-accepted limitations of impedance spectroscopy in practical sensors for trace analyte detection include relatively low sensitivity and prohibitively long acquisition times over the broad frequency range. Embodiments described herein enhance the ability to measure changes in properties of the irreversible sensing material by putting the material onto the electrodes of the resonant LCR sensor circuit. Similarly, the disclosed embodiments enhance the ability to measure changes in properties of the fluid in proximity to the electrodes of the resonant LCR sensor circuit. Experimental testing examined the effects of changing dielectric constant on sensing electrodes both with and without a resonator. Compared to the conventional impedance spectroscopy, the bare resonant LCR sensor provided an at least 100-fold enhancement in the signal-to-noise (SNR) over the smallest measured range of $\Delta\in$ with the corresponding improvement of detection limit of dielectric constant determinations.

Performance of the LCR sensor as analyzed using multivariate analysis tools provides an advantage of improved selectivity over the processing of individual responses of individual sensors. In particular, test results indicate the relations between $F_p$ and $Z_p$ and the relations between calculated sensor resistance R and calculated sensor capacitance C have much less selectivity between responses to different vapors or fluids as compared to the relations between multivariable parameters that show more variation, as discussed in detail below. Further, the LCR sensors demonstrate independent contact resistance and contact capacitance responses that improve the overall selectivity of the multivariable response of the LCR sensors. This selectivity improvement originates from the independent contributions of the contact resistance and contact capacitance responses to the equivalent circuit response of the sensor.

Diverse irreversible sensing materials may be advantageously utilized on the sensing region of the LCR resonant sensor because analyte-induced changes in the irreversible sensing material film affect the impedance of the antenna LCR circuit through the changes in material resistance and capacitance, contact resistance and capacitance between the transducer and irreversible sensing material, and resistance and capacitance between the transducer substrate and irreversible sensing material. Such changes provide diversity in response of an individual RFID sensor and provide the opportunity to replace an entire array of conventional sensors with a single LCR or RFID sensor.

Non-limiting examples of irreversible sensing materials include conjugated polymers, carbon nanotubes, organometallic complexes, enzymatic systems, metallic films, nanoparticle films, metal organic frameworks, nanocomposites, a combination of a dielectric material and a semiconducting material, a combination of the dielectric material and a conducting material, a combination of a polymer and a metal salt, a combination of a plurality of the polymers and the metal salt, a combination of a polymer and an organic metal complex, or any combination thereof. The use of these materials provides the ability to tailor the relative direction of sensing response upon exposure to vapors of different natures. The different partition coefficients of vapors into these or other irreversible sensing materials further modulate the diversity and relative direction of the response.

In combination with a dielectric polymer (non-limiting examples include silicones, poly(etherurethane), polyisobutylene siloxane fluoroalcohol, etc.), conjugated polymer (polyaniline, polythiophene, poly(vinyl ferrocene), poly(fluorene)-diphenylpropane), poly(3,4-ethylenedioxythiophene) polypyrrole, bilypyrrole) or any other material (non-limiting examples include porphyrins, metalloporphyrins, metallophthalocyanines, carbon nanotubes, semiconducting nanocrystals, metal oxide nanowires) that responds to analyte adsorption with more pronounced changes in capacitance or resistance, a sensor with a wider range of analyte responses is developed. Other examples of materials that may be combined with the exemplary irreversible sensing materials are described in U.S. Patent Publication No. 2012/0116683 entitled "Highly Selective Chemical and Biological Sensors," which is incorporated herein by reference.

In certain embodiments, when the irreversible sensing material is a metallic film, the material may undergo irreversible changes in conductivity or resistivity upon exposure to the analyte. In other words, electrical properties of the metallic film, such as dielectric property, conductivity, or resistivity, may decrease or increase if exposed to the analyte. In one embodiment, a calcium metallic film may react with air or oxygen to become oxidized and less conductive. In further embodiments, a metal organic framework may be able to trap gases and act as the gas dosimeter.

In other embodiments, an enzymatic system, which may be part of a larger system, may be used as the dosimeter in the RFID system. These embodiments may include catalase, which can transform hydrogen peroxide into water and oxygen. Thus, the enzyme may be used in a system that includes an irreversible sensing material that changes its dielectric properties upon water exposure (e.g., a hydrogel) or a moiety may be redox active (e.g., ferrocene or ferrocyanide) and changes the dielectric constant of the overall film. The enzymatic system may also include metal-centered proteins that can perform redox reactions in situ in the presence of the suitable analytes or co-factors. Examples of such enzymatic systems include, but are not limited to, copper superoxide dismutase (SOD) systems, peroxide systems, oxidase systems, and so forth.

In further embodiments, using a preconcentration of vapors, the sensing device or system may include a nanocomposite capable of detecting analytes in a dosimeter fashion. Examples include a nanocomposite made of a surface functionalized carbon nanotube and a conducting polymer for detecting organic or inorganic gases. In certain embodiments, the irreversible sensing material may include a preconcentrator.

In certain embodiments, the irreversible sensing material may include several components. For example, the irreversible sensing material may include an inactive matrix and one or more active additives. The inactive matrix may also be referred to as an inert matrix or inert polymer matrix. In addition, the inactive matrix may be used to help support the one or more active additives. For example, the one or more active additives may be dispersed within the inactive matrix. Examples of the inactive matrix include, but are not limited to, aliphatic polyether-based thermoplastic polyurethanes or any other inert matrix material, including a polymer matrix material. The electrical properties of the one or more active additives may change irreversibly during analyte sensing.

In certain embodiments, each of the active additives may include an active polymer and a dopant. The dopant may also be referred to as a metal salt, a metallic ion dopant, or a metallic ion salt. An example of the active polymer includes, but is not limited to, polyaniline, which may exist in several different oxidation states, such as leucoemeraldine, emeraldine, or (per)nigraniline. The dopant may be a soluble metallic ion salt, such as, but not limited to, copper (II) acetate, zinc acetate, copper (II) chloride, iron (II) acetate, palladium chloride, or any combination thereof. As discussed below, the concentration of the dopant may be varied to adjust the sensitivity of response of the irreversible sensing material.

A multivariate dosimeter sensor may be a sensor that has a single sensing material region that is probed with at least two transduction techniques, such as capacitive readout and resistive readout. A nonlimiting example of such a multivariate dosimeter sensor may be a RFID sensor that includes at least two components where the first component is an integrated circuit (IC) memory chip for storing and processing information and modulating and demodulating a radio frequency signal. The second component of the RFID tag is an antenna for receiving and transmitting the radio frequency signal. The memory chip of this RFID tag may contain at least two inputs for an analog signal. Nonlimiting examples of an analog signal include resistance, capacitance, inductance, or optical signals. The analog signals may be generated by a resistive transducer, a capacitive transducer, an inductive transducer, a work function transducer, a mass transducer, or an optical transducer. In certain embodiments, the multivariate dosimeter sensor may include a first transducer and a second transducer, which may be different from one another (e.g., the first transducer may be a resistive transducer and the second transducer may be a capacitive transducer). The at least two inputs of the memory chip may be used to receive a first analog signal from the first transducer and a second analog signal from the second transducer. In other embodiments, the multivariate dosimeter sensor may include three or more transducers. In certain embodiments, the memory chip of this RFID tag may contain at least three inputs for an analog signal, such as a resistance input, a capacitance input, an inductance input, or other types of inputs. The sensing material may be disposed on the RFID sensor that is connected to the memory chip. The sensing material may provide either an irreversible or a reversible response to an analyte of interest.

In certain embodiments, a sensing material may be disposed on both the first and second transducers that are different from one another. For example, the same sensing material may be disposed on both a resistive transducer and a capacitive transducer. In other words, certain embodiments do not include different sensing materials disposed on the first and second transducers, which may be found in "electronic nose" sensor arrays where different sensing materials respond differently to diverse chemicals in the environment. Applying the same sensing material onto different transducers is not widely used because a response of a sensing material using one transducer does not guarantee a response of the same sensing material using a different transducer. Instead, often a sensing material responds well using one transducer and responds poorly using a different transducer. Thus, the successful use of the same sensing material disposed on first and second transducers that are different from one another in multivariate dosimeter sensors is unexpected.

In another embodiment, an environment or sample may be in contact with or in proximity to both the first and second transducers that are different from one another. For example, the same environment may be in contact with both a resistive transducer and a capacitive transducer. Having the same environment or sample in contact with or in proximity to different transducers is not widely used because often an environment responds well when measured with one transducer and responds poorly when measured with a different transducer. Thus, the successful use of the same environment or sample in contact with the first and second transducers that are different from one another in multivariate dosimeter sensors is unexpected.

In various embodiments, the multivariate dosimeter sensor may be wireless, wired, electronic, RFID (radio frequency identification) based, non-RFID based, or any combination thereof. In embodiments where the sensor is a RFID based sensor, the sensor may be a wireless sensor. In addition, embodiments of the RFID based sensor may include a passive RFID tag, a semi-passive RFID tag, or an active RFID tag. Further, the RFID tags may be configured to operate at various frequency ranges, such as, but not limited to, a low frequency range from about 125 KHz to about 135 KHz, a high frequency range of about 13.56 MHz, an ultra high frequency (UHF) range from about 850 MHz to about 960 MHz, and a microwave frequency range of about 2.45 GHz to about 5.8 GHz.

In one embodiment, sensors are embedded into or onto packaging labels, tickets, or banknotes. In another embodiment, sensors are embedded into or onto disposable or re-usable consumer products. In a further embodiment, sensors have chips with a memory size ranging from about 1 bit to about 1 gigabyte of memory.

Sensors may be interrogated (measured) with sensor readers that can obtain analog or digital information from the sensors. Nonlimiting examples of devices with incorporated sensor readers for reading the sensor response include a residential device, an industrial device, a home remote control, a home appliance, an industrial appliance, a device not connected to the network, a device connected to the network, a stationary device, a mobile device, a device for public security and protection, a medical device, an industrial safety device, a food safety device, a desktop device, a pocket-size device, and an embedded device.

Nonlimiting examples of communication modes for reading the sensors include Wi-Fi™, Bluetooth™, Zigbee™, near field communication (NFC), inductive coupling, capacitive coupling, optical coupling, card emulation, tag reading, peer-to-peer, high-frequency (HF) communication, ultrahigh-frequency (UHF) communication, ISO 15693, ISO 14443, ISO 18000-1, ISO 18000-2, ISO 18000-3, ISO 18000-4, ISO 18000-5, ISO 18000-6, ISO, 18000-6C, and ISO 18000-7.

Nonlimiting examples of communication implementations include stand-off detection at distances ranging from about 1 meter to about 1000 kilometers, proximity detection at distances ranging from about 1 micrometer to about 1 meter, and non-galvanic contact detection in a "tapping" scenario for a short period of time or in a non-galvanic attachment scenario for a relatively long period of time.

A multivariate dosimeter sensor may be a sensor that is a standalone sensor node and is a part of a sensor network. Individual sensors can be arranged into a sensor network where sensors communicate with each other and with the central station or only with the central station. In particular, individual sensors may be arranged into a wireless sensor network (WSN). In a WSN, individual sensors are typically arranged into wireless sensing nodes (also known as motes) with the key hardware (long-lifetime battery or energy harvesting source, simple signal conditioning components, low-power processor) and software (small needed memory, computational capacity, high modularity) requirements for individual nodes. The arrangement of individual wireless sensors into a distributed network poses certain challenges. For example, challenges associated with using WSNs for gas and physical sensing include power consumption of individual sensors and handling of massive heterogeneous data from the WSN. The inadequate selectivity of existing gas sensors further prevents their reliable application in WSNs.

The opportunities for WSNs with gas sensing nodes originate from the synergistic combination of new data-generation and processing concepts with new sensor-integration concepts. Sensors arranged as networks can significantly benefit from novel data-generation and processing concepts currently unavailable for individual sensors. Three main aspects of these advantages are (1) the ability for efficient sensor communications, (2) improvement of detection accuracy through data fusion, and (3) opportunities for automatic re-calibration of individual sensors on the network.

The broad opportunities for WSNs originate from the capabilities based on concepts of integration of individual sensors to form sensing nodes in a WSN. Indeed, a stationary or mobile origin of sensing nodes would dictate the diversity of application scenarios for a WSN. Significant advantages in the reliability and accuracy of a WSN performance is achieved upon an integration of sensing nodes into a component or a system that already has a maintenance schedule that is matched to a maintenance schedule for sensing nodes.

As a result of developments in the data-generation/processing and sensing node-integration concepts, the application concepts for WSNs can be broadly described as those that rely on (1) stationary sensing nodes for mapping of chemical sources, (2) mobile sensing nodes for dynamic localization of chemical sources, (3) real-time chemical condition monitoring of high-value goods and their associated storage conditions, and (4) combination of sensing nodes with an intelligent inventory management.

The key features of wireless sensor networks exist in at least two areas, such as (1) data-generation and processing concepts and (2) sensor-integration concepts. In the area of data-generation and processing concepts, key WSN features include:
1. Implementation of available infrastructure for communications of sensors;
2. Heterogeneous sensors coupled to multiparameter coincidence techniques to improve detection accuracy;
3. Fusion and processing strategies for massive and dynamic data from WSNs for time-critical decision-making and for providing ability to identify spurious signals and malfunction of individual sensors on the network;
4. Data acquisition algorithms for individual sensors to reduce power consumption and to extend operational lifetime before battery replacement;
5. Auto-calibration methods for maintenance-free operation of individual gas sensors in WSN. Responses of sensors are calibrated against local reference monitoring stations; and
6. Internet-enabled pollution monitoring server interfaced to Google Maps™ mapping service to display real time pollutants levels and locations in large metropolitan areas.

In the area of sensor-integration concepts, key WSN features include:
1. Integration of sensors into mobile phones;
2. Autonomous sensor- and GPS-equipped mobile robotic devices for location and validation of pollution, homeland security threat, and other sources; and
3. Integration of sensors into public or personal transportation vehicles for pollution and homeland security threat monitoring with a significant benefit of matching vehicle/sensor maintenance schedules.

In certain embodiments, irreversible response in wireless sensors is induced by patterning of the sensing films and promoting dewetting and coalescence effects of these patterned films. Dewetting is a process when a relatively thin spread film on a substrate breaks and forms relatively thick droplets. Coalescence is the process by which separate bodies of substances (e.g., islands of a film on a surface or droplets) pull each other together upon an initial contact and merge into one body which is typically thicker than initial individual bodies of substances that were pulled together. The patterning is established by a variety of known techniques with nonlimiting examples that include self-assembly of sensing polymeric and composite nanobeads, guided growth of polymeric structures on surface-functionalized nanopatterns, electrostatic lithography for polymeric patterns, electropolymerization techniques, self-assembled block copolymer lithography, dewetting and coalescence technique for highly ordered arrays of nanowires, electrospinning techniques, and polymer imprint lithography with single-walled carbon nanotubes as templates. The feature sizes of the patterns range from more than about 500 nm to about 2 nm.

To increase sensitivity of dosimeter response of the films to small concentrations of analytes, structured films are deposited onto a sensor surface that is pretreated to alter substrate surface energy to promote sensor film surface delamination at small analyte concentrations. Dewetting and coalescence effects can also be utilized to produce useful chemical dosimeters when the morphology of a thin sensing film is altered upon vapor exposure.

Control of the irreversible response may be provided by an irreversible chemical reaction where, in a nonlimiting example, reaction products are volatile and are removed from the dosimeter film during reaction. Control of the irreversible response may also provided by an irreversible physical change of the reaction products that include precipitation, aggregation, acid-base reaction, donor-acceptor complex formation, dewetting, coalescence, clustering, oxidation, reduction, and corrosion. Control of the irreversible response may further be provided by an irreversible morphological change and dissolution change of the sensing material.

In one embodiment the readout is performed with an analog sensor or a digital RFID sensor. The analog sensor provides the response from the resonant sensing structure, such as a LCR resonator. The digital sensor provides the response from the RFID IC memory chip structure that has an analog input from a separate sensor.

Figure 5:
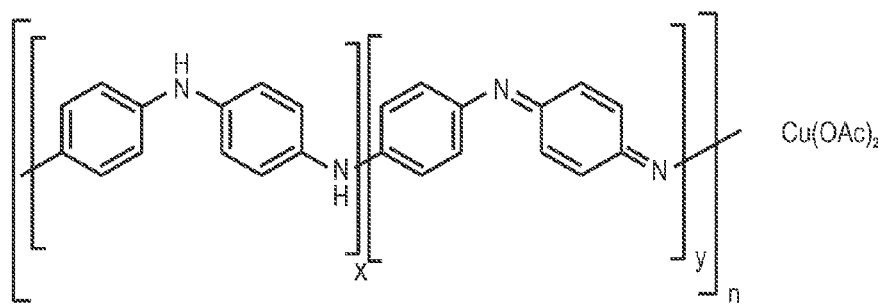
FIG. 5 illustrates an irreversible sensing material, in accordance with embodiments of the invention.

Together, the inactive matrix, active polymer, and the dopant may be formed as a film, such as the film of polyurethane, polyaniline emeraldine, and copper (II) acetate shown in FIG. 5. Embodiments of the irreversible sensing material that include a combination of the inactive matrix, the active polymer, and the dopant may have a synergetic effect compared to combinations that do not include one or more of these components. Specifically, combinations of the inactive matrix, the active polymer, and the dopant may have increased sensitivity, increased signal response, and decreased noise than may be expected.

When the film shown in FIG. 5 is used in a gas dosimeter, the following mechanism may occur. First, divalent copper may form sulfide organometallic complexes on the surface of the irreversible sensing material (i.e., the dielectric constant changes). Second, upon exposure to the analyte, such as hydrogen sulfide, metal sufide species may be formed. Third, the emeraline base of the polyaniline emeraldine may be protonated by the weak acid formed upon exposure to the analyte. Thus, the electrical properties of the irreversible sensing material change irreversibly in response to exposure to the analyte.

Figure 6:
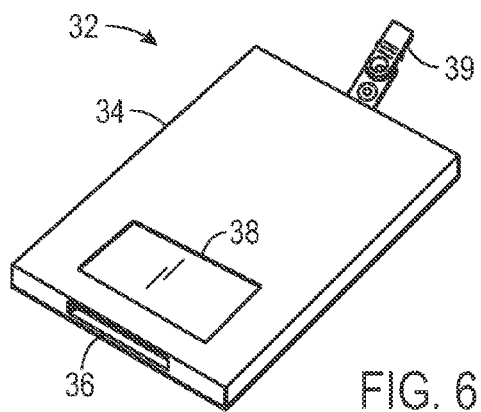
FIG. 6 illustrates a perspective view of a gas dosimeter that includes an irreversible sensing material.

The irreversible sensing material may be used in gas dosimetry in a variety of ways. As shown in FIG. 6, a gas dosimeter 32 may include a housing 34 that encloses a multivariate sensor that includes the irreversible sensing material. The housing 34 may include an opening 36 to admit the analyte and enable the irreversible sensing material to be exposed to the analyte. Thus, the multivariate sensor may determine a concentration of the analyte over time. Specifically, the electrical properties of the irreversible sensing material may change irreversibly upon exposure to the analyte. In certain embodiments, the housing 34 may include a display 38 configured to display the concentration of the analyte over time. In other embodiments, the housing 34 may include a clip 39 to allow the gas dosimeter 32 to be worn by personnel. In further embodiments, tubing may be used to actively or passively convey a vapor to the opening 36 of the housing 34. For example, a fan or similar device may be used to convey the vapor to the gas dosimeter 32.

Irreversible sensing materials exhibit analyte responses, which can be described by one or more of three response mechanisms of LCR or RFID sensors, such as resistance changes, dielectric constant changes, and swelling changes. A composite irreversible sensing material can be constructed which incorporates the exemplary coordination compounds with multiple different individual irreversible sensing materials, which each respond to analytes by predominantly different response mechanisms. Such composite irreversible sensing materials produce an enhanced diversity in the multivariate response. Such composite irreversible sensing materials may be homogeneously or inhomogeneously mixed or locally patterned over specific portions of the LCR resonator.

Further, in order to avoid potentially deleterious effects of disparate materials on each other in a composite irreversible sensing material (e.g. high dielectric constant medium suppressing conduction in a conductive filler material), the material components are chosen to locally phase separate due to hydrophylic/hydrophobic interactions or mutual immiscibility, allowing the different mechanisms active in each component to be sensed by the sensor. In another embodiment, a composite irreversible sensing material can be formed as sectors of individual materials deposited adjacent to each other onto a single sensor. In another embodiment, a composite irreversible sensing material can be formed as layers of individual materials deposited on top of each other onto a single sensor.

To further improve selectivity of response, overcoating of sensing films with auxiliary membrane filter films may be performed. Non-limiting examples of these filter films include zeolite, metal-organic framework, and cavitand filters.

These diverse irreversible sensing materials shown as non-limiting examples are provided on the sensing region of the LCR or RFID resonant sensor because analyte-induced changes in the irreversible sensing material film affect the impedance of the antenna LCR circuit through the changes in material resistance and capacitance, contact resistance and capacitance between the transducer and irreversible sensing material, resistance and capacitance between the transducer substrate and irreversible sensing material. Such changes provide diversity in response of an individual RFID sensor and provide the opportunity to replace a whole array of conventional sensors with a single LCR or RFID sensor, as illustrated further below, with regard to EXPERIMENTAL DATA.

EXPERIMENTAL DATA

Resonant antenna structures, such as those described above, were used for demonstration of the disclosed techniques. Various irreversible sensing materials were applied onto the resonant antennas by conventional draw-coating, drop coating, and spraying processes. Measurements of the impedance of the RFID sensors were performed for example with a network analyzer (Model E5062A, Agilent Technologies, Inc., Santa Clara, Calif.) under computer control using LabVIEW. The network analyzer was used to scan the frequencies over the range of interest (i.e., the resonant frequency range of the LCR circuit) and to collect the impedance response from the RFID sensors.

For gas sensing, different concentrations of vapors were generated using an in-house built computer-controlled vapor-generation system. Collected impedance data was analyzed using KaleidaGraph (Synergy Software, Reading, Pa.) and PLS Toolbox (Eigenvector Research, Inc., Manson, Wash.) operated with Matlab (The Mathworks Inc., Natick, Mass.).

EXAMPLE

Detection of $H_2S$

Figure 7:
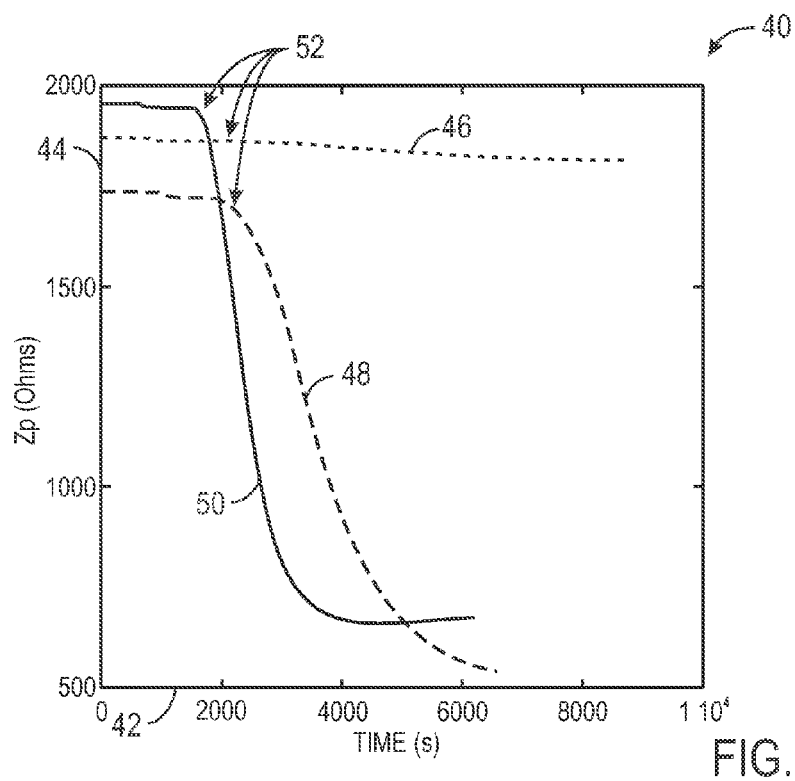
FIGS. 7-9 illustrate test data demonstrating a single sensor capable of irreversibly measuring low concentrations of hydrogen sulfide, in accordance with embodiments of the invention.
Figure 8:
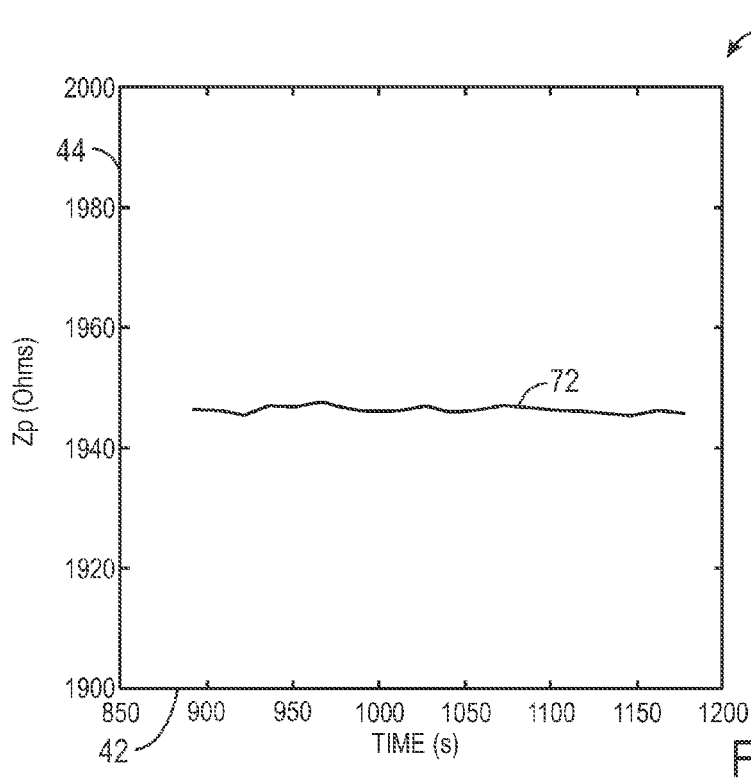
Figure 9:
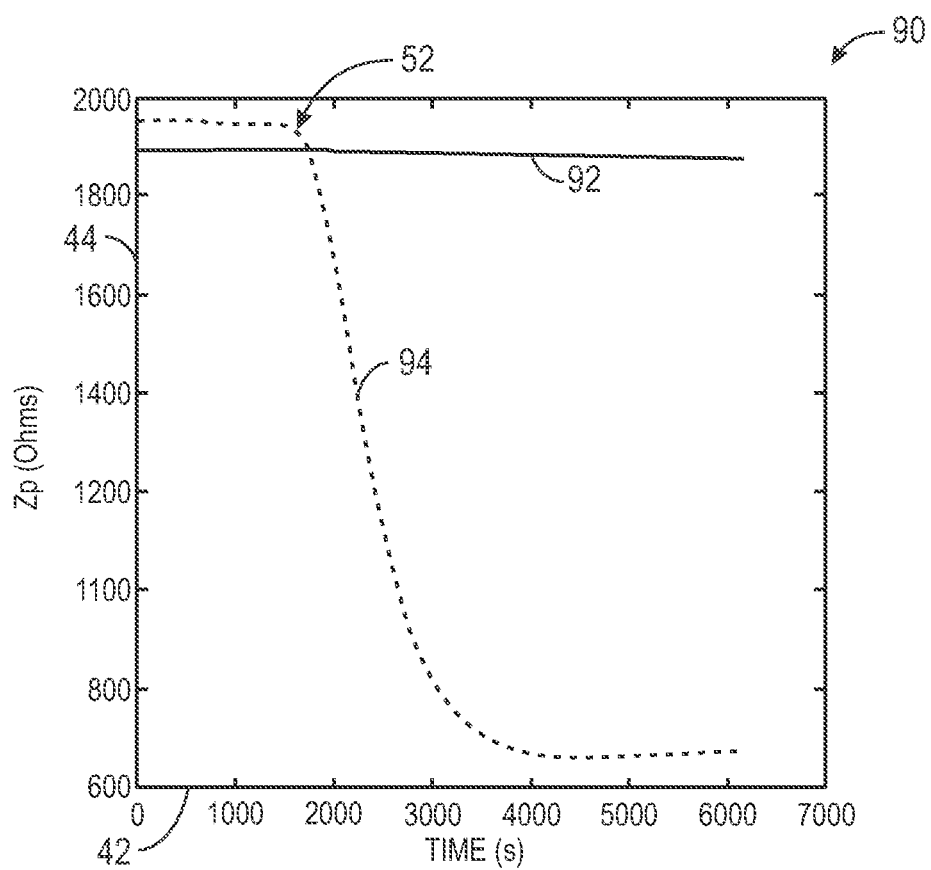

As illustrated in FIGS. 7-9, test results were obtained to demonstrate the selective detection of $H_2S$ using a single sensor, such as the sensor 12 described above. Specifically, 10 ppm $H_2S$ was formed upon addition of acetic acid (20 µL)

to an aqueous solution of Na$_2$S (sodium sulfide) in water (30 µL aliquot of 4.0 g in 470 mL solution) in a 1 L box, which contained the sensor. Sulfide contents of the starting solution and final solutions were determined using a Chemets total sulfide kit (Chemetrics, Calverton, Va.).

The irreversible sensing material used to coat the RFID tag was carefully chosen and provided the ability to selectively detect H$_2$S. In the present experiment, the chosen irreversible sensing material was polyaniline emeraldine base (PANI/EB)/polyurethane (PU)/Cu(OAc)$_2$, which was applied as a sensing film onto an RFID sensor chip by spray coating. Specifically, the irreversible sensing material was synthesized as follows.

Polyurethane pellets (Tecoflex 80A from The Lubrizol Corporation, Wickliffe, Ohio) (250 mg) were dissolved in warm methylene chloride (48 mL) for 0.25-3 hours and cooled down for 20 minutes. A suspension of polyaniline emeraldine salt (2 wt % in xylenes) was then added to the resulting solution to form a green solution. A 1 mM ethanolic solution of the soluble metal acetate was added (1 mL) to a solution of the corresponding polymer suspension (6 mL of polymer solution and 7 mL of methylene chloride) and stirred for 1 hour. The formulation was then spray coated as a thin film onto polyethylene inlays (AD 709 from Avery Dennison Corporation, Pasadena, Calif.). The resulting sensing RFID device was then treated with a solution of ammonium hydroxide (30% aqueous) by dip coating and left to dry overnight under inert atmosphere before conducting the sensing experiments.

As illustrated in the graph 40 of FIG. 7, experimental data demonstrated that the sensor with a thin film of polyaniline emeraldine base (PANI/EB)/polyurethane (PU)/Cu(OAc)$_2$ based formulation was able to detect 10 ppm of H$_2$S. As shown in FIG. 7, an x-axis 42 represents time in seconds and a y-axis 44 represents the impedance ($Z_p$) in ohms To serve as a control, a first curve 46 represents the response of a sensor with a thin film of polyaniline emeraldine base (PANI/EB)/polyurethane (PU) based formulation (e.g., without the dopant Cu(OAc)$_2$). A second curve 48 represents the response of the sensor with a thin film of polyaniline emeraldine base (PANI/EB)/polyurethane (PU)/Cu(OAc)$_2$ based formulation. A third curve 50 represents the response of the same sensor with a thin film of polyaniline emeraldine base (PANI/EB)/polyurethane (PU)/Cu(OAc)$_2$ based formulation when the experiment was duplicated. Exposure of the sensor to the H$_2$S began at points 52 in FIG. 7. In other words, the H$_2$S began to be evolved from the addition of the acetic acid to the aqueous solution of Na$_2$S at the points 52.

As shown in FIG. 7, the second and third curves 48 and 50 correspond to a gas dosimeter response. In other words, the impedance ($Z_p$) began to decrease steadily as the sensor continued to be exposed to the H$_2$S until the sensor reached a point of saturation (e.g., after approximately 6500 seconds for the second curve 48 and after approximately 4250 seconds for the third curve 50). Thus, the measured impedance ($Z_p$) may correspond to a concentration of the H$_2$S over time. For comparison, the first curve 46 (i.e., the control) shows a negligible chance in impedance ($Z_p$) upon exposure to the H$_2$S. In addition, the level of detection of the responses shown in FIG. 7 was calculated with a signal to noise ratio (S/N) of 3 and was determined to be 5.4 ppb for the detection of 10 ppm of H$_2$S gas in the 1 L headspace of the experiment.

One convenient way of analyzing various responses of the sensor is to use principal components analysis (PCA) to produce a multivariate signature. As will be appreciated, PCA analysis is a mathematical process, known to those skilled in the art, that is used to reduce multidimensional data sets to lower dimensions for analysis. FIG. 8 represents a graph 70 of the results of further processing results of multivariate processing of the sensing data shown in FIG. 7. A fourth curve 72 indicates a standard deviation of approximately 0.6, showing good resolution of different vapors with a single sensor.

Based on experimental testing, Cu(OAc)$_2$ was determined to be the most effective dopant for H$_2$S detection. In addition, the concentration of the dopant may be varied to adjust or tune the sensitivity of the irreversible sensing material. A thin film of PU/PANI (EB) was used as the control and showed no response to H$_2$S, as represented by line 46 shown in FIG. 7. In addition, the irreversible sensing material showed no response to the interferent acetic acid (AcOH). For example, FIG. 9 shows a graph 90 of experimental data collected using the sensor with a thin film of polyaniline emeraldine base (PANI/EB)/polyurethane (PU)/Cu(OAc)$_2$ based formulation to detect 200 ppm of H$_2$S in the presence of acetic acid. Specifically, a fifth curve 92 represents the acetic acid and a sixth curve 94 represents the response of the sensor. As shown in FIG. 9, the fifth curve 94 appears generally unaffected by the presence of the acetic acid. In other words, the shape and response of the sixth curve 94 is analogous to the shape and response of the second and third curves 48 and 50 shown in FIG. 7.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A gas dosimeter, comprising:
   a housing configured with an opening to admit an analyte; and
   a multivariate sensor disposed in the housing, wherein the sensor is configured to determine a concentration of the analyte over time, the multivariate sensor comprising an irreversible sensing material, wherein electrical properties of the irreversible sensing material are configured to change irreversibly upon exposure to the analyte, wherein the irreversible sensing material comprises an inactive matrix and an active additive, wherein the active additive comprises an active polymer and a dopant, wherein the dopant is configured to react with the analyte and form a reaction product upon exposure to the analyte, and wherein the reaction product is configured to react with the active polymer to irreversibly change the electrical properties of the irreversible sensing material.

2. The gas dosimeter of claim 1, wherein the inactive matrix comprises a polymer.

3. The gas dosimeter of claim 1, wherein the active polymer comprises polyaniline.

4. The gas dosimeter of claim 1, wherein the dopant comprises copper (II) acetate, zinc acetate, copper (II) chloride, iron (II) acetate, palladium chloride, or any combination thereof.

5. The gas dosimeter of claim 1, wherein the irreversible sensing material comprises a preconcentrator.

6. The gas dosimeter of claim 1, comprising a filter layer disposed adjacent the irreversible sensing material, wherein the filter layer is configured to enable passage of the analyte through the filter layer to the irreversible sensing material, block passage of interferences through the filter layer to the irreversible sensing material, or any combination thereof.

7. The gas dosimeter of claim 1, wherein the multivariate sensor comprises an RFID sensor, and the irreversible sensing material is disposed on a resonant antenna of the RFID sensor, across the resonant antenna and a memory chip of the RFID sensor, on the RFID sensor that is connected to the memory ship, or any combination thereof.

8. The gas dosimeter of claim 1, wherein the irreversible sensing material comprises conjugated polymers, carbon nanotubes, organometallic complexes, enzymatic systems, metallic films, nanoparticle films, metal organic frameworks, nanocomposites, a combination of a dielectric material and a semiconducting material, a combination of the dielectric material and a conducting material, a combination of a polymer and a metal salt, a combination of a plurality of the polymers and the metal salt, a combination of a polymer and an organic metal complex, or any combination thereof.

9. The gas dosimeter of claim 1, wherein the analyte comprises hydrogen sulfide, sulfur dioxide, arsine, ammonia, hydrogen peroxide, methanethiol, hydrogen bromide, hydrogen chloride, hydrogen iodide, hydrogen fluoride, hydrogen cyanide, chlorine dioxide, oxygen, chlorine, phosgene, bromine, carbon dioxide, carbon monoxide, trinitrotoluene, triacetone triperoxide, explosives, or any combination thereof.

10. A multivariate sensor, comprising:
an irreversible sensing material, comprising:
  a first matrix configured to provide a first output indicative of the concentration of an analyte over time; and
  a second matrix configured to provide a second output to correct for environmental interference effects, wherein electrical properties of the irreversible sensing material are configured to change irreversibly upon exposure to the analyte; and
wherein the first matrix comprises a first inactive matrix and a first active additive, wherein the first active additive comprises a first active polymer and a first dopant, wherein the first dopant is configured to react with an analyte and form a reaction product upon exposure to the analyte, and wherein the reaction product is configured to react with the first active polymer to irreversibly change the electrical properties of the irreversible sensing material.

11. The multivariate sensor of claim 10, wherein the second matrix comprises a second inactive matrix and a second active additive.

12. The multivariate sensor of claim 11, wherein the second active additive comprises a second active polymer and a second dopant.

13. The multivariate sensor of claim 10, wherein the multivariate sensor comprises a resonant circuit, an RFID sensor, a multivariable sensor transducer, or any combination thereof.

14. The multivariate sensor of claim 10, wherein the electrical properties of the irreversible sensing material comprise dielectric properties, dimensional properties, charge transfer properties, a complex impedance of the sensor resonance, or any combination thereof.

15. A multivariate dosimeter sensor, comprising:
at least two transducers configured to generate at least two signals;
an irreversible sensing material disposed on the at least two transducers, wherein the irreversible sensing material comprises an inactive matrix and an active additive, wherein the active additive comprises an active polymer and a dopant, wherein the dopant is configured to react with an analyte and form a reaction product upon exposure to the analyte, and wherein the reaction product is configured to react with the active polymer to irreversibly change electrical properties of the irreversible sensing material; and
an RFID device comprising an integrated circuit chip configured to receive the at least two signals.

16. The multivariate dosimeter sensor of claim 15, wherein the at least two transducers comprise capacitive transducers, resistive transducers, inductive transducers, work function transducers, mass transducers, optical transducers, or any combination thereof.

17. The multivariate dosimeter sensor of claim 16, comprising at least three transducers configured to generate at least three signals, wherein the irreversible sensing material is disposed on the at least three transducers, and the at least three transducers comprise capacitive transducers, resistive transducers, inductive transducers, work function transducers, mass transducers, optical transducers, or any combination thereof.

18. The multivariate dosimeter sensor of claim 16, wherein the reaction product is configured to react with the active polymer to irreversibly change electrical properties of the irreversible sensing material via an irreversible chemical reaction that generates additional reaction products, and control of the irreversible response is provided by precipitation, aggregation, acid-base reaction, donor-acceptor complex formation, dewetting, coalescence, clustering, oxidation, reduction, or corrosion of the additional reaction products, or irreversible morphological change or dissolution change of the irreversible sensing material.

19. A multivariate dosimeter sensor node, comprising:
a first transducer configured to generate a first signal;
a second transducer configured to generate a second signal;
an irreversible sensing material disposed on both the first transducer and the second transducer, wherein the irreversible sensing material comprises an inactive matrix and an active additive, wherein the active additive comprises an active polymer and a dopant, wherein the dopant is configured to react with an analyte and form a reaction product upon exposure to the analyte, and wherein the reaction product is configured to react with the active polymer to irreversibly change electrical properties of the irreversible sensing material; and
an RFID device comprising an integrated circuit chip configured to receive the first and second signals.

20. The multivariate dosimeter sensor node of claim 19, wherein the multivariate dosimeter sensor node comprises a standalone sensor node and is part of a sensor network.

21. The multivariate dosimeter sensor node of claim 19, wherein the first and second transducers comprise capacitive transducers, resistive transducers, inductive transducers, work function transducers, mass transducers, optical transducers, or any combination thereof, and the first and second transducers are different from one another.

* * * * *